(12) United States Patent
Hendriks et al.

(10) Patent No.: US 8,812,132 B2
(45) Date of Patent: Aug. 19, 2014

(54) TEMPERATURE CONTROL OF PATIENTS DURING SURGERY

(75) Inventors: Bernardus Hendrikus Wilhelmus Hendriks, Eindhoven (NL); Liesbeth van Pieterson, Heeze (NL); Gerhardus Wilhelmus Lucassen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 906 days.

(21) Appl. No.: 12/440,071

(22) PCT Filed: Sep. 20, 2007

(86) PCT No.: PCT/IB2007/053825
§ 371 (c)(1),
(2), (4) Date: Dec. 8, 2009

(87) PCT Pub. No.: WO2008/038198
PCT Pub. Date: Apr. 3, 2008

(65) Prior Publication Data
US 2010/0094385 A1  Apr. 15, 2010

Related U.S. Application Data

(60) Provisional application No. 60/826,814, filed on Sep. 25, 2006.

(51) Int. Cl.
*A61F 7/00* (2006.01)
(52) U.S. Cl.
USPC .......................................................... 607/100
(58) Field of Classification Search
USPC .......................................... 607/100; 219/211
See application file for complete search history.

(56) References Cited

U.S. PATENT DOCUMENTS

| 4,832,029 | A  | * | 5/1989 | Koch et al. ............... 607/100 |
| 4,969,459 | A  |   | 11/1990 | Gusakov |
| 5,977,517 | A  | * | 11/1999 | Grosjean ................. 219/211 |
| 6,719,780 | B1 | * | 4/2004 | Salmon et al. ............. 607/108 |
| 2003/0040783 | A1 | * | 2/2003 | Salmon .................... 607/108 |
| 2003/0211797 | A1 | * | 11/2003 | Hill et al. ................. 442/205 |
| 2005/0177093 | A1 | * | 8/2005 | Barry et al. ............... 604/20 |
| 2006/0282134 | A1 | * | 12/2006 | Shapiro et al. ............ 607/88 |

FOREIGN PATENT DOCUMENTS

| DE | 4012854 | 10/1990 |
| DE | 4014770 | 11/1990 |
| DE | 4113803 | 10/1992 |
| DE | 29509405 | 1/1996 |
| DE | 29811137 | 10/1998 |
| EP | 0619995 | 4/1994 |
| EP | 1086673 | 3/2001 |

(Continued)

*Primary Examiner* — Linda Dvorak
*Assistant Examiner* — Daniel Fowler

(57) ABSTRACT

An infrared radiant heating system for raising or maintaining a uniform core temperature of the body of a patient during surgery, substantially without affecting the temperature of the area surrounding the patient's body, includes an infrared radiant heater located near the patient to provide radiant heat to the entire body or one or more parts of the body of the patient. The system further includes a controller in communication with the heater for controlling the intensity level and distribution of intensity of the radiant heat on the patient's body such that the skin temperature of the patient's body is raised or maintained within a predetermined range resulting in the uniform core body temperature, substantially without affecting the temperature of the area surrounding the patient's body.

4 Claims, 3 Drawing Sheets

(56) References Cited

FOREIGN PATENT DOCUMENTS

| GB | 1462033 | 1/1977 |
|---|---|---|
| RU | 94020018 | 5/1996 |
| RU | 23360 | 6/2002 |
| WO | WO03021596 | 3/2003 |
| WO | WO03022189 | 3/2003 |
| WO | WO03095729 | 11/2003 |
| WO | WO2005011491 | 2/2005 |
| WO | WO2006129272 | 12/2006 |

* cited by examiner

TEMPERATURE CONTROL OF PATIENTS DURING SURGERY

CROSS REFERENCE TO RELATED CASES

Applicants claim the benefit of International Application Number PCT/IB2007/053825, filed Sep. 20, 2007, and Provisional Application Ser. No. 60/826,814, filed Sep. 25, 2006.

The disclosure is directed to an infrared radiant heating system for raising or maintaining a uniform temperature of the body of a patient during surgery, substantially without affecting the temperature of the area surrounding the patient's body.

In the operating room during surgery (which can typically last for several hours), the temperature is usually set at a level which is convenient for the surgeon, typically around 20 degrees Celsius. For the patient this temperature is too low, and therefore undesirable, for several reasons. First, during surgery, the interior of the body portion of the patient at the site of the surgery is open and exposed, thereby causing a loss of body heat to the atmosphere and resulting in a lowering of the patient's body temperature. Second, patients are not covered with thick clothes since this would interfere with the doctor being able to successfully perform the surgical procedure, again resulting in a cooling down of the patient during surgery.

To keep the patient warm during surgery, various methods have been previously employed. For example, heating the mattress on the operating table has the drawback that the patient is heated up on one side only. Furthermore, the patient may lay on the mattress for an extended period of time during surgery, resulting in pressure points, which in combination with the heating, can cause injuries to the patient. Another method for warming the patient involves the use of a heating blanket, which again only heats one side of the body and is not very convenient for performing surgery. Another method involves blowing warm air on the patient. A drawback of this is that it can disturb the sterilization atmosphere in an operating room during surgery. For some operations sterilized air flows down from above to create a more sterilized surrounding of the patient. The blowing of warm air disturbs this. Still another method involves the use of a heat shield, which is bulky and not convenient to use.

Additionally, various heating apparatus have been suggested for use in warming the patient during surgery, some of which are convection heaters. However, such apparatus have been inefficient or not effective due to their bulkiness, interference with the surgical team's ability to perform the surgery, or inability to uniformly heat the entire patient body.

These and other needs are satisfied with the infrared radiant heating system and method of use of the present disclosure.

According to the present disclosure, an infrared radiant heating system for raising or maintaining a uniform core temperature of the body of a patient during surgery, substantially without affecting the temperature of the area surrounding the patient's body, is disclosed.

Specifically, it is an object of the invention to provide an infrared radiant heating system for raising or maintaining a uniform core temperature of the body of a patient during surgery, substantially without affecting the temperature of the area surrounding the patient's body, comprising:
  infrared radiant heating means which in use is located in an unobtrusive position near the patient to provide radiant heat to the entire body or one or more parts of the body of the patient;
  and control means in communication with the heating means for controlling the intensity level and distribution of intensity of the radiant heat on the patient's body such that in use the core temperature of the patient's body is raised or maintained within a predetermined range resulting in the uniform core body temperature, substantially without affecting the temperature of the area surrounding the patient's body.

Another object is to provide a system wherein the infrared heating means further comprises a pixelated array of infrared light illuminating devices which are incorporated into an illumination system of an operating room where the surgery is to be conducted.

Another object is to provide a system wherein the infrared light illuminating devices comprise light emitting diodes.

Another object is to provide a system wherein the control means further comprises temperature sensing means adapted to sense skin temperature at a plurality of positions of the patient's body, thereby causing the control means to control the radiant heat intensity level and distribution of the heating means to raise or maintain the skin temperature of the patient's body within the predetermined range.

Another object is to provide a system wherein the infrared heating means are embedded throughout surgical clothing worn by the patient during surgery; and the control means further comprises temperature sensing means embedded throughout the clothing and adapted to sense skin temperature at a plurality of positions of the patient's body, thereby causing the control means to control the radiant heat intensity level and distribution of the heating means to raise or maintain the skin temperature of the patient's body within the predetermined range.

Another object is to provide a system wherein the infrared heating means are releasably attached throughout surgical clothing worn by the patient during surgery; and the control means further comprises temperature sensing means releasably attached throughout the clothing and adapted to sense skin temperature at a plurality of positions of the patient's body, thereby causing the control means to control the radiant heat intensity level and distribution of the heating means to raise or maintain the skin temperature of the patient's body within the predetermined range.

Another object is to provide a system wherein the predetermined skin temperature range is from about 37° C. to 41° C. and the core temperature is about 37.5° C.

Another object is to provide a method of raising or maintaining a uniform core temperature of the body of a patient during surgery, substantially without affecting the temperature of the area surrounding the patient's body, using an infrared radiant heating system comprising:
providing the system comprising:
  infrared radiant heating means which in use is located in an unobtrusive position near the patient to provide radiant heat to the entire body or one or more parts of the body of the patient; and
  control means in communication with the heating means for controlling the intensity level and distribution of intensity of the radiant heat on the entire patient's body such that in use the skin temperature of the patient's body is raised or maintained within a predetermined range resulting in the uniform core body temperature, substantially without affecting the temperature of the area surrounding the patient's body;
positioning the heating means in an unobtrusive manner near the patient; and
controlling the heating means such that the skin temperature of the patient's body is raised or maintained within a predetermined range, substantially without affecting the temperature of the area surrounding the patient's body.

Another object is to provide a method wherein the infrared heating means further comprises a pixelated array of infrared light illuminating devices which are incorporated into an illumination system of an operating room where the surgery is to be conducted.

Another object is to provide a method wherein the infrared light illuminating devices comprise light emitting diodes.

Another object is to provide a method wherein the control means further comprises temperature sensing means adapted to sense skin temperature at a plurality of positions of the patient's body, thereby causing the control means to control the radiant heat intensity level and distribution of the heating means to raise or maintain the skin temperature of the entire patient's body within the predetermined range.

Another object is to provide a method wherein the infrared heating means are embedded throughout surgical clothing worn by the patient during surgery; and the control means further comprises temperature sensing means embedded throughout the clothing and adapted to sense skin temperature at a plurality of positions of the patient's body, thereby causing the control means to control the radiant heat intensity level and distribution of the heating means to raise or maintain the skin temperature of the patient's body within the predetermined range.

Another object is to provide a method wherein the infrared heating means are releasably attached throughout surgical clothing worn by the patient during surgery; and the control means further comprises temperature sensing means releasably attached throughout the clothing and adapted to sense skin temperature at a plurality of positions of the patient's body, thereby causing the control means to control the radiant heat intensity level and distribution of the heating means to raise or maintain the skin temperature of the patient's body within the predetermined range.

Another object is to provide a method wherein the predetermined skin temperature range is from about 37° C. to 41° C. and the core temperature is about 37.5° C.

These and other aspects of the invention are explained in more detail with reference to the following embodiments. FIGS. 1-3 are reproduced from European Patent Application 05104703.3 filed on May 31, 2005 hereby incorporated by reference in its entirety.

In this invention we propose to use infrared (IR) radiant light illuminating devices which are designed such that only the body of the patient is radiated/illuminated. The infrared light illumination causes a more uniform heating up of the patient. Furthermore, the heating up is more efficient since IR light penetrates deeper in the skin resulting in a less steep temperature profile in the skin than that occurs with heating by convection, and thereby a uniform core body temperature (optimally about 37.5° C.). Since the IR radiation is well confined to the area of the patient and is absorbed, the area around the patient remains almost unaffected (hence the surgical team does not suffer from it).

For example, in one embodiment, the IR radiant heating means/light source is incorporated in the illumination system of the operating room. Using several IR light sources that can be tuned in intensity, a well defined illumination area can be defined as well as the intensity distribution within this area. In this way the patient can be heated up uniformly. Preferably the IR heating means is in the form of a pixelated array, for example, a pixelated LED array, with each LED having a heat energy output of up to about 500 milliwatts. LEDs are more efficient than light bulbs and they produce the correct spectrum of light. More particularly, IR LEDs produce substantially only non-visible IR light in the invention herein. The illumination system is typically in a fixed ceiling position above the operating table where the patient's body lies. Alternatively, for a ceiling position, other IR light sources can be used, for example, an array of halogen lamps which can be controlled separately to produce a pixelated light distribution.

Figure 5:
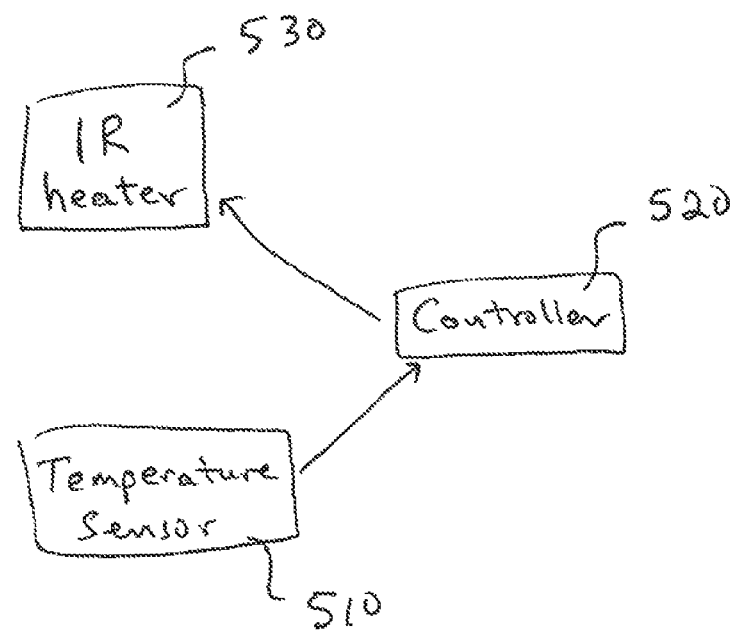
FIG. 5 is an illustration of an embodiment of the invention showing a controller for controlling an IR radiant heater based on temperature detected by a temperature sensor.

The intensity level and intensity distribution of the IR radiation can be addressed manually or can be controlled by a feedback loop. In the latter case various ways can be envisioned. For example as shown in FIG. 5, the temperature of the patient is measured by heat or temperature sensors 510 located at various sites on the skin of the patient's body. This information is communicated to and processed by the control means 520 which, in turn, controls the IR radiant heating means 530 to provide the proper IR intensity level and distribution of intensity level over the patient's body to raise or maintain a uniform skin temperature of the patient's body within a predetermined range.

Alternatively, an IR camera can be used to measure the temperature of the patient. Again, the control means would process this information in controlling the radiation intensity level and distribution of the IR radiant light coming from the IR radiant heating means.

Figure 4:
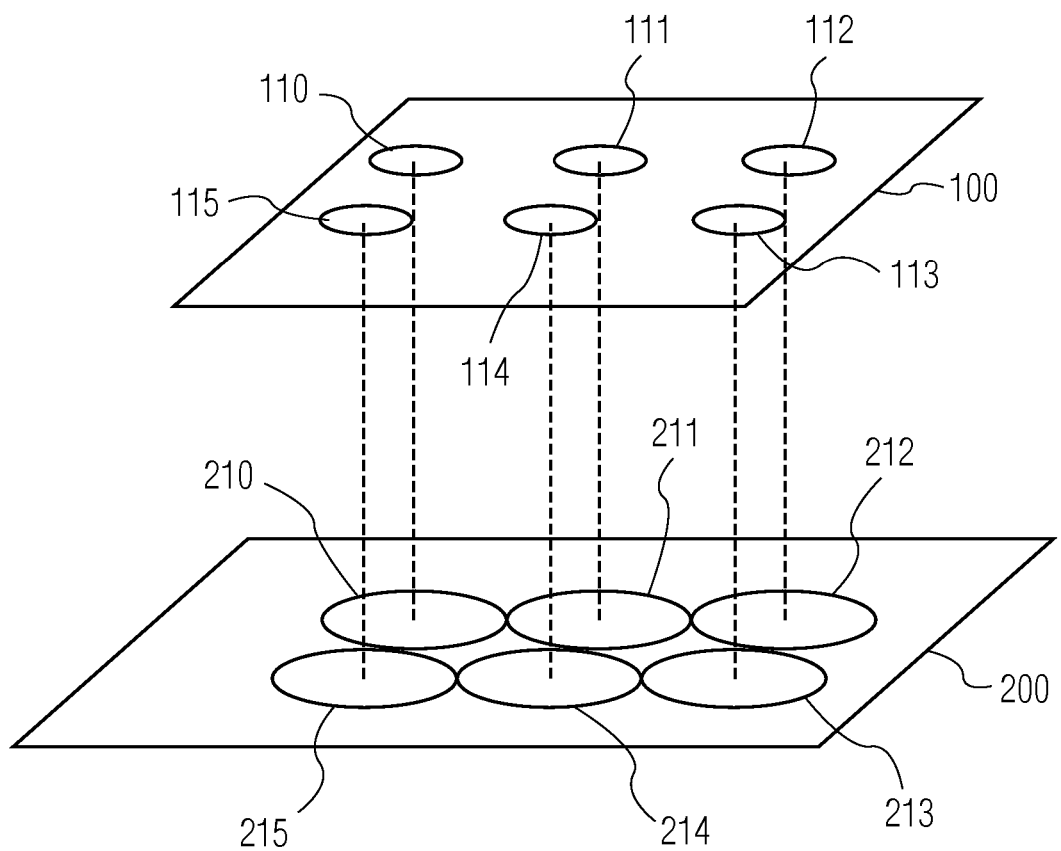
FIG. 4 is an illustration of an embodiment of the invention depicting an independently addressable array of IR light sources positioned above an operating table.

For example, as is shown in FIG. 4, an array of IR light sources 100 consisting of IR light sources 110-115 produces light distributions 210-215, respectively. By switching on/off the IR light source separately and independently, the array illuminated on the operation table 200 can be adjusted. An additional detection system, for example, a camera, detects the position of the patient and that of the surgeon. The light distribution is adjusted such that the patient is illuminated while the surgeon is not. Furthermore, a further control loop, for example a PID temperature controller, is used which measures the skin and/or core temperature of the patient and adjusts the IR light intensity accordingly such that the core temperature of the patient remains substantially constant, for example, about 37.5° C.

For example, in another embodiment, by incorporating the IR radiant heating means/light sources in the clothing material the patient wears during the operation, a uniform IR illumination of the patient's body is possible. The clothing can be equipped with temperature/heat sensors that communicate with a control means for controlling the illumination intensity level and distribution emanating from the IR radiant heating means. The light source can be IR light emitting diodes (LED). An example of a woven electrode array for LEDs is described more completely in recently filed European Patent (EP) Application 05104703.3, filed May 31, 2005, entitled "A Fully Textile Electrode Lay-out Allowing Passive and Active Matrix Addressing", and corresponding International Patent Application Number PCT IB2006/051716 filed May 30, 2006, both of which are hereby incorporated by reference in their entirety herein.

According to the EP 05104703.3, in one embodiment, such clothing can be made of woven textile having a multilayer structure, and is preferably made with at least a double layer structure. The textile may be woven from yarns in a first direction, which may be termed the warp direction, interwoven with yarns aligned in a second direction, which may be termed the weft direction. Yarns in the weft direction traverse the yarns in the warp direction. The warp and weft directions are transverse to one another and preferably substantially orthogonal to one other.

It is to be understood that the terms "warp" and "weft" are used simply in relation to the directions lengthwise and crosswise on a textile sheet, but are not necessarily used to imply any limitation on a method of fabricating a textile on a weaving loom.

The term "multi-layer warp" is used to encompass a textile in which a plurality of layers of warp yarns are used to weave a single textile piece, being distinct from multi-layer textiles formed from separately woven pieces.

Optoelectronic devices can be attached to the textile on either or both faces. Such devices can have two, three, four or more electrodes that need to be connected to the textile. Exemplary embodiments will be given for one-, two-, and three-colour light emitting diodes (LEDs), however the principles outlined are intended to be suitable for other types of devices. Besides light emitting modules, any suitable kind of electronic component may be attached, such as sensors 28 shown in FIG. 2, actuators, driver integrated circuits and the like. In the case of two- and three-colour LEDs, shared anodes he indicated.

Different types of yarns and/or fibres may be used: electrically conductive yarns and electrically non-conductive yarns. Both types of yarn may be of single or multifilament type. If using multi-filament yarns, a degree of twist may be necessary in the yarn in order to prevent short circuits between adjacent multi-filament yarns due to electrical connections between stray single yarn filaments.

Conductive yarns according to the invention are defined as those which have an electrically conductive material on at least an outer surface of the yarn. Such yarns may be of various types of construction, and may for example have an internal core of another material. The internal core may include a non-conductive material. Non-conductive yarns according to the invention are defined as having at least a non-conducting outer surface, and may be made entirely from non-conductive material or may have a conductive core.

Any suitable fibres or yarns may be used for the conductive and non-conductive yarns. For example, copper, stainless steel or silver plated polyamide fibres may be used for the conductive yarns. Nylon, cotton or polyester fibres could be used for the non-conductive yarns.

A number of weave structures are possible based on the type of LED to be used, for example whether the LED is to be a single or multiple (bi/tri) colour type. The number of layers in the weave structure may depend on the type and grade of yarn used and the pitch of the weave. Preferably the number of layers in the warp direction is two, but more layers may be used without departing from the scope of the invention. In the illustrated embodiments, only one layer in the weft direction is shown, but more than one layer may be used without departing from the scope of the invention.

Figure 1:
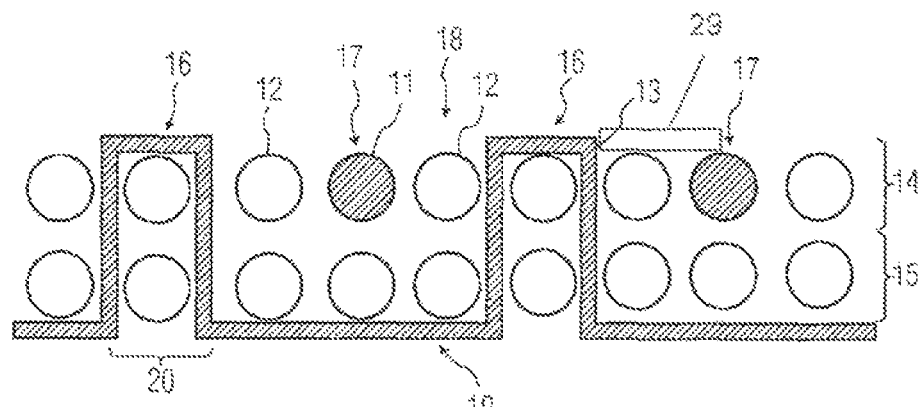
FIG. 1 illustrates a schematic cross-sectional view along a weft axis of an example single sided matrix for a single color LED with a double layer 1×3 twill weave.

Referring to FIG. 1, an example embodiment is shown in the form of a schematic cross-sectional view of a single sided matrix based on a double layer twill weave. The expression 'single sided matrix' is used to indicate that conductive warp and weft yarns for connection of electrical components appear on only one surface of the textile. This is suitable for the attachment of single colour LEDs 29 on to one side of the woven structure at anode electrode connection 16 and cathode electrode connection 17. It will be understood that, according to design choice, the 'anode' and 'cathode' connection designations could be reversed.

In FIG. 1 and subsequent figures the warp yarns are indicated in cross-section by circles, where filled circles indicate electrically conductive yarns 11 and open circles indicate non-conductive yarns 12. The solid lines 13 indicate the conductive weft yarns, which run transverse relative to the warp yarns. In FIG. 1, only a first layer 14 of warp yarns contains conductive yarns 11. A second layer 15 of warp yarns contains only non-conductive warp yarns. The weft yarns may consist of a plurality of conductive weft yarns 13 and non-conductive weft yarns (not shown). The number n of conductive weft yarns 13 typically determines the number of separately addressable lines in the warp direction. The number m of conductive warp yarns 11 typically determines the number of separately addressable lines in the weft direction. In this example therefore up to n×m separately addressable single colour LEDs may be attached to the textile within the area of the textile created by the repeat weave pattern shown in FIG. 1.

The weave shown in FIG. 1 is a 1×3 twill weave on a first surface 18, and a 3×1 twill weave on a second surface 19. Each conductive warp yarn 11 has at least two neighbouring non-conductive warp yarns 12 in the same layer. Electrical contact between adjacent conductive warp yarns 11 and the interlacing conductive weft yarn 13 is prevented by means of interposing non-conductive warp yarns 12. In this example adjacent conductive warp yarns 11 are separated by at least three non-conductive warp yarns 12. Each conductive weft yarn 13 has at least two neighbouring parallel non-conducting weft yarns so that there is no electrical contact between adjacent conductive weft yarns.

It is to be understood that the non-conducting weft yarns in all embodiments and examples described herein do not necessarily follow the same paths as the conducting weft yarns as they are woven around and between conducting and non-conducting warp yarns.

The electrically conductive weft yarn 13 in FIG. 1 traverses the warp between the non-conducting warp yarns. This traversal involves the transition of a weft yarn 13 from one face of the textile 19 through the multi-layer warp, passing through the second warp layer 15 and first warp layer 14, to the opposite face 18 of the textile.

Two successive traversals of a conductive weft yarn through the textile, in which the conductive weft yarn 13 passes around at least one warp yarn in at least one, and preferably all, layers of the multi-layer warp, forms a loop 20. In FIG. 1 the loop 20 encompasses a total of two non-conductive warp yarns in the first and second layers 14, 15 of warp yarns. The loop 20 forms the anode electrical connection 16 on the first surface 18 of the textile, while a proximal portion 17 of the conductive warp yarn 11 forms the cathode electrical connection.

Figure 2:
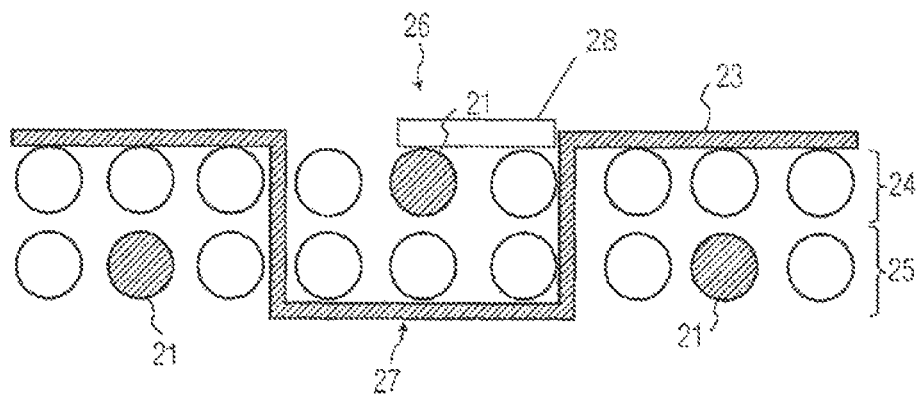
FIG. 2 illustrates a schematic cross-sectional view along a weft axis of an example double sided matrix for a single color LED with a double layer 3×3 twill weave.
Figure 3:
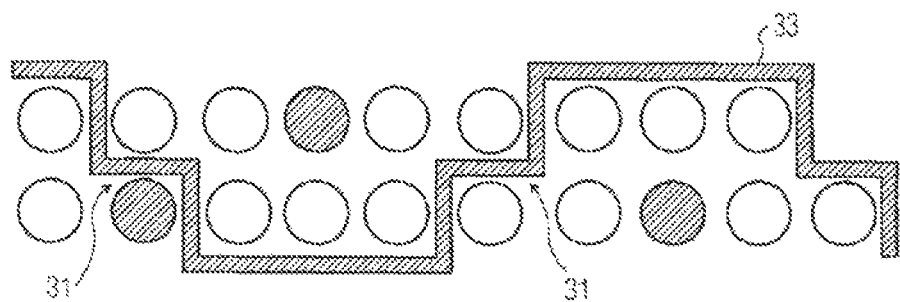
FIG. 3 illustrates a schematic cross-sectional view along a weft axis of an example double sided matrix for a single color LED with a double layer 3×5 twill weave containing floats in the central plane.

FIGS. 2 and 3 illustrate two examples of weave structures for a double-sided matrix that allows for single colour LED attachments. The expression 'double sided matrix' is used to indicate that conductive warp and weft yarns for connection of electrical components appear on both surfaces of the textile.

These examples are also in the form of double layer weaves containing a first layer of warp yarns 24 and a second layer of warp yarns 25, with an interlacing conductive weft yarn 23. In these double-sided matrix arrangements both the first layer 24 and second layer 25 of warp yarns contain conductive warp yarns 21. These conductive warp yarns 21 are also disposed on alternating faces 26, 27 of the textile in the first layer 24 and the second layer 25 respectively of the multi-layer warp, which in this example has only two layers. The weave structure in FIG. 3 also contains floats 31 formed by the conductive weft yarn 33 in the central plane, i.e. the plane between the first layer 24 and second layer 25 of warp yarns. These floats 31 are formed by the passing of the weft yarn 33 between two adjacent warp yarns in different planes of the multi-layer warp. Their function is, in this case, to improve the integrity of the woven structure by reducing the number of warp yarns which the conductive weft yarn 33 crosses from one traversal to a successive traversal.

In order to allow connection of multiple colour LEDs to the woven fibre matrix extra conductive warp yarns are needed, one for each cathode. Again, adjacent conductive warp yarns are separated by at least one interposing non-conductive warp yarn so that there is no electrical contact between adjacent conductive warp yarns, and between the conductive warp yarns and the interlacing conductive weft yarns. Adjacent conductive weft yarns are also separated by at least one non-conductive weft yarn so that there is no electrical contact between the adjacent conductive weft yarns.

The textile may, in addition to electronic components such as LEDs, incorporate a radio frequency antenna comprising woven conductive yarns in electrical connection with and for remote communication with the electronic components. The antenna may be in the form of a coil comprising electrically conducting warp and weft yarns. Remote communication may be enabled via the driving circuitry. The antenna may be used to provide a communications link with remote control equipment. Such remote control equipment may provide signals to the antenna, which signals can then be translated by the driving circuitry into other signals, which other signals then drive the electronic components attached to the textile. Alternatively, or in addition, the antenna may transmit signals from the textile to the remote control equipment. Such transmitted signals may comprise information received by the driving circuitry from one or more electronic components attached to the textile, such as temperature, light or other sensors. It is also understood that techniques well known to one skilled in the art, other than weaving of electronic circuitry in textiles as above described, can be used. Such techniques can include, for example, utilizing embroidery, printing, and electroplating a substance and then etching the circuit thereon.

A useful predetermined skin temperature range, for example is about 37 to 41 degrees centigrade (° C.), which generally correlates with a normal core body temperature of about 37.5 degrees centigrade. The temperature of the skin surface varies from anatomical site but is roughly between 32 and 35 degrees centigrade. The assumption here is that body temperature is raised through IR radiation penetrating the body. This means that to obtain a constant body temperature the predetermined temperature should be a few degrees higher but never close to pain threshold level, which may vary from person to person usually between 41 to 45 degrees centigrade. The body will irradiate and conduct heat to its environment which lowers the temperature. The IR radiation source must compensate for this loss and keep body temperature constant in a closed loop system. This can be accomplished using a feedback loop with a temperature sensor that generates a signal to regulate the heating device by means of the difference between sensor temperature and actual temperature, for example, using a PID (Proportioanal-Integra-Derivative) control system. Such system are very well known.

The present invention may be employed in one of two modes. Firstly, it may be used to initially raise the core temperature of a patient. In this case the skin temperature might be set using the control means to range between about 37° C. and 41° C., or more narrowly between 39° C. and 41° C. In this mode there will be a positive net energy transfer between the environment and the patient resulting in patient's core temperature rising. Once the patient's core temperature has reached an acceptable level the present invention may be employed in a second mode whereby it is used to maintain the core temperature of the patient. In this case the skin temperature might be set using the control means, for example at 37.5° C. which would result in a roughly zero net energy transfer between the patient and the environment. In this case the radiant warmer is only compensating for the heat losses of the patient.

Temperature sensing means are well known and include, for example, ear thermometer devices, IR sensing devices, skin contact temperature sensors, etc.

While the present invention has been described with respect to specific embodiments thereof, it will be recognized by those of ordinary skill in the art that many modifications, enhancements, and/or changes can be achieved without departing from the spirit and scope of the invention. Therefore, it is manifestly intended that the invention be limited only by the scope of the claims and equivalents thereof.

The invention claimed is:

1. An infrared radiant heating system for raising or maintaining a uniform core temperature of a body of a patient during surgery, comprising:
    infrared radiant heaters which in use are located near the patient to provide radiant heat to the body or one or more parts of the body of the patient, wherein the infrared radiant heaters include a first set of heaters attached to electrodes woven throughout clothing worn by the patient during surgery and a second set of heaters incorporated into an illumination system of an operating room where the surgery is to be conducted;
    temperature sensors attached to further electrodes woven throughout the clothing and configured to sense the skin temperature at a plurality of positions of the patient's body;
    a controller in communication with the infrared radiant heaters and the temperature sensors, wherein the controller is configured to control an intensity level and a distribution of intensity of the radiant heat on the patient's body from the first set of heaters and from the second set of heaters such that in use a skin temperature of the patient's body is raised or maintained within a predetermined range as sensed by the temperature sensors; and
    a detector configured to detect a position of the patient and subjects near the patient, wherein the controller is further configured to adjust the intensity level and the distribution of intensity of the radiant heat from the second set of heaters to avoid heating the subjects detected by the detector.

2. The system of claim 1, wherein the predetermined range is from about 37° C. to 41° C. and the core temperature is about 37.5° C.

3. The system of claim 1, wherein
    the electrodes include a first set of electrodes woven in a first direction and a second set of electrodes woven in a second direction different from the first direction, the first set of electrodes forming a loop consisting of non-conductive yarn between sections of the clothing including the second set of electrodes and further non-conductive yarn.

4. The system of claim 1, wherein the electrodes include a first set of electrodes woven in a first direction in two layers and a second set of electrodes woven in a second direction different from the first direction, the second set of electrodes having portions parallel to each other including first and second portions along exposed surfaces of the two layers and a third portion between the two layers.

* * * * *